(12) United States Patent  
Claudon

(10) Patent No.: US 9,599,549 B2
(45) Date of Patent: Mar. 21, 2017

(54) SYSTEM AND PROCESS FOR CHARACTERIZATION OF THE OPERATION OF WATER RETENTION DEVICE

(71) Applicant: General Electric Company, Schenectady, NY (US)

(72) Inventor: Philippe Claudon, Etueffont (FR)

(73) Assignee: General Electric Company, Schenectady, NY (US)

( * ) Notice: Subject to any disclaimer, the term of this patent is extended or adjusted under 35 U.S.C. 154(b) by 270 days.

(21) Appl. No.: 14/500,604

(22) Filed: Sep. 29, 2014

(65) Prior Publication Data

US 2015/0090015 A1    Apr. 2, 2015

(30) Foreign Application Priority Data

Sep. 30, 2013    (FR) ...................................... 13 59405

(51) Int. Cl.
*G01N 15/02* (2006.01)
*B01D 45/08* (2006.01)
*B01D 46/00* (2006.01)

(52) U.S. Cl.
CPC ............. *G01N 15/02* (2013.01); *B01D 45/08* (2013.01); *B01D 46/003* (2013.01); *G01N 15/0255* (2013.01)

(58) Field of Classification Search
CPC ...... B01D 45/08; B01D 46/003; G01N 15/02; G01N 15/0255
See application file for complete search history.

(56) References Cited

U.S. PATENT DOCUMENTS

2013/0276514 A1    10/2013    Claudon

FOREIGN PATENT DOCUMENTS

DE    29907077 U1    7/2000
FR    2964574 A1    3/2012

OTHER PUBLICATIONS

French Republique, INPI National Industrial Property institute, Search Report and Written Opinion for Application No. FR1359405 mailed Jul. 1, 2014, 8 pages.
English Translation of French Republique Search Report for Application No. FR1359405 mailed Jul. 1, 2014, 2 pages.

*Primary Examiner* — Francis Gray
(74) *Attorney, Agent, or Firm* — Ernest G. Cusick; Hoffman Warnick LLC

(57) ABSTRACT

A system for characterizing a water retention device may include a test pipe including a mount section for holding the water retention device to be tested; an injector to inject, upstream of the mount section, an air flow loaded with at least one of dust and droplets of water; at least one sensor for determining a distribution of sizes of the at least one of the dust and water particles, and a quantity of water retained in the mount section; and a calculator receiving the measured distribution of dust and water particles delivered by the at least one sensor to determine therefrom a dust and water retention level in the water retention device.

14 Claims, 3 Drawing Sheets

SYSTEM AND PROCESS FOR CHARACTERIZATION OF THE OPERATION OF WATER RETENTION DEVICE

This application claims priority under 35 USC 119 to French National Patent Application No. 1359405, filed Sep. 30, 2013.

BACKGROUND OF THE INVENTION

Embodiments of the invention concern the control of performance of water retention devices, particularly those installed or intended to be fitted upstream of gas turbines.

As used herein, "water retention device" includes a device configured to stop the water droplets in an air flow from crossing the device. Furthermore, it includes coalescers, separators of droplets by inertia, or through baffles.

The coalescer devices are necessary in surroundings with a high concentration of humidity in the air, in order to remove humidity. A coalescer operates by trapping the small droplets of water in the fibers. The water particles captured combine with other particles to form larger drops of water. The coalescers are designed either to allow the droplets to flow towards the bottom of the device by gravity, or in a manner that they are released in the airflow current in order to be captured downstream by a separator.

In a turbine, the droplets of water contained in the air inflow are likely to damage the compressor blades. Thus, a water retention device is placed upstream of the turbine to prevent the entry of the droplets of water in the compression phases.

A problem occurs due to the fact that the water retention device, whose function is to stop the droplets of water contained in an airflow, also stops a part of the dust particles contained in the flow. This causes the device to clog and increases the related impedance loss. This impedance loss may lead to the shutdown of the turbine.

To compensate for this inconvenience, one must arrange a water retention device in a manner that it is capable of fulfilling its main function, i.e., stopping the droplets of water, while capturing the least possible amount of dust particles.

BRIEF DESCRIPTION OF THE INVENTION

Embodiments of the invention provide a system and a process that allow characterizing the operation of a water retention device, particularly concerning the retention of dust particles and droplets of water.

A first aspect provides a system for characterization of a water retention device, comprising: a test system for a water retention device, the system comprising: a test pipe including a mount section for holding the water retention device to be tested; an injector to inject, upstream of the mount section, an air flow loaded with at least one of dust and droplets of water; at least one sensor for determining a distribution of sizes of the at least one of the dust and water particles, and a quantity of water retained in the mount section; and a calculator receiving the measured distribution of dust and water particles delivered by the at least one sensor to determine therefrom a dust and water retention level in the water retention device.

Through such a system, it is possible to characterize a water retention device by its dust and water retention level, i.e., a set of information comprising the distribution of sizes and quantity of these particles retained by the device.

Preferably, an injector loads the airflow with dust and droplets of water. The dust and/or droplets of water is/are placed in the test pipe located upstream of the mount section of the water retention device.

Thus, the air flow in the pipe can easily be loaded with dust and droplets of water. Furthermore, the quantity of dust loaded in the water retention device is directly related to the quantity of dust loaded in the airflow.

In one embodiment, the methods of injection may include a mist system placed in the test pipe upstream of the mount section of the water retention device.

The airflow upstream of the mount section of the water retention device may easily be loaded with droplets of water, according to the quantities that the user may control.

In an embodiment, the measurement sensors may include a sensor capable of measuring the distribution of sizes of dust and water particles in the test pipe.

In an embodiment, the pipe comprises a first group of drains upstream of the mount section and a second group of drains downstream of the mount section.

In another embodiment, the water retention device to be tested is intended to be placed in a vertical position.

In another embodiment, the water retention device is intended to be placed in a horizontal position. In an embodiment, the test pipe comprises an inlet filter and/or an outlet filter. In this manner, the air inflow and air outflow are devoid of dust particles.

Another aspect may include a process of characterization of a water retention device, through a test system as defined herein, comprising the following steps: disposing the water retention device in the mount section of the test pipe; subjecting the water retention device to an airflow loaded with at least one of dust particles and droplets of water; determining a distribution of sizes of dust particles and droplets of water in the airflow before and after the water retention device, and a quantity of water retained in the water retention device in the mount section, and calculating a dust and water retention level of the water retention device.

In one embodiment, the step of submitting the water retention device to an airflow loaded with dust and droplets of water includes submitting the device to an airflow loaded only with dust, or to an airflow loaded only with droplets of water.

In an embodiment, the device is weighed before and after the step of submission to the airflow, and the calculating includes calculating the difference between these two mass measurements for determining the quantity of water retained.

The step for determining the distribution of sizes of particles may include measurement upstream and downstream of the device in order to determine the distribution of sizes of particles retained in the device.

Thus, the quantity and the distribution of sizes of dust particles and water retained by the device can be determined during the characterization of the process.

BRIEF DESCRIPTION OF THE DRAWINGS

These and other features of the invention will be detected on examination of the detailed description taken in conjunction with the accompanying drawings that depict various embodiments of the invention, in which.

DETAILED DESCRIPTION OF THE INVENTION

Figure 1:
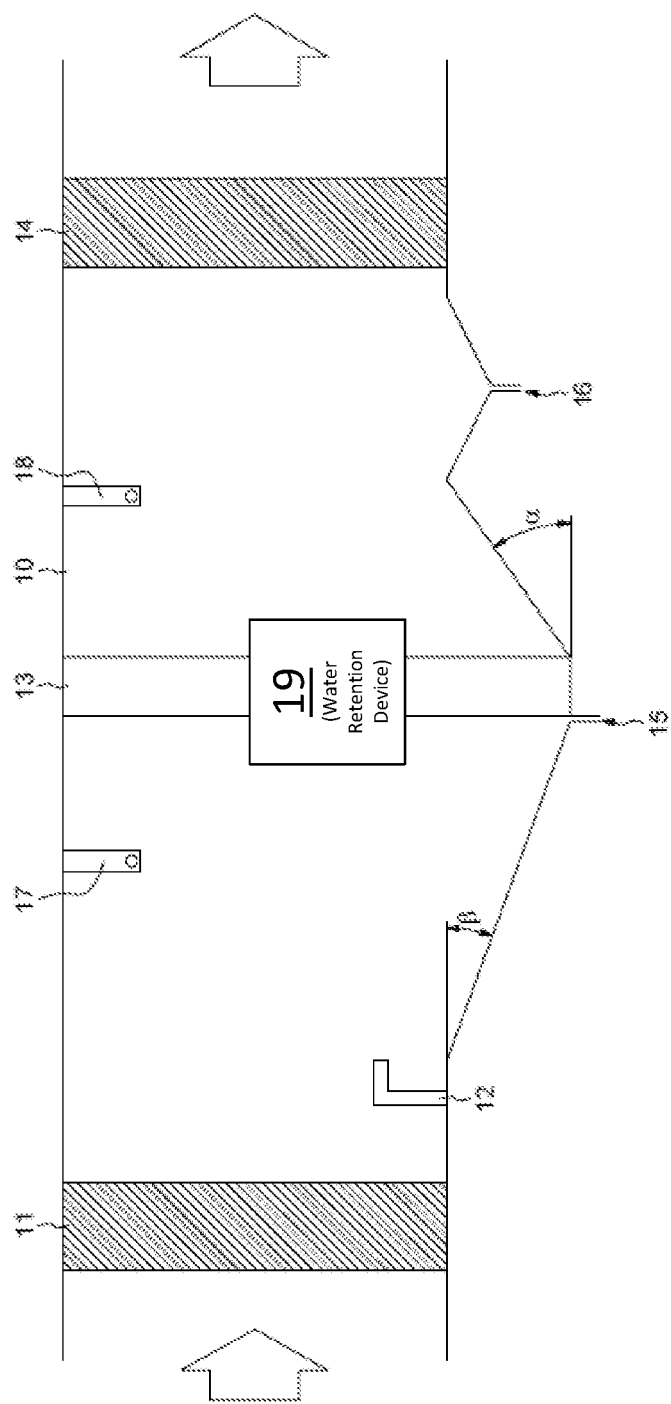
FIG. 1 represents a schematic view of a system for characterization of a water retention device according to a first embodiment.

FIG. 1 schematically represents a sectional view of a system for characterization of a water retention device 19 according to a first embodiment.

The test system includes a test bench used to characterize a water retention device 17. In one embodiment, it may characterize the operation of a coalescer device. For example, it may characterize a coalescer device placed upstream of a compressor of a gas turbine. However, it will be understood that the teachings of the invention may be applied for controlling the efficiency of filtration of another type of water retention device.

As seen in FIG. 1, the system comprises a test pipe 10 in which is maintained an airflow loaded with dust particles and/or droplets of water. Thus, this test pipe is in open circuit but it may very well constitute a closed circuit by air recirculation. A fan or similar device for circulating the air is at the origin of the airflow.

The pipe 10 may include an inlet filter 11. This filter is intended, during operation of the test bench, to filter the air inflow in the pipe in order to have clean air upstream of the injection section.

Downstream of the inlet filter 11 is located a mount section 13 for holding the water retention device 19 to be tested. In this example, the water retention device 19 in the form of the coalescer device may be fitted vertically. In one non-limiting example, the coalescer device may be placed in a manner that it forms an angle with the vertical line. In particular, the coalescer device may be brought up to forming an angle with the 45° vertical line, clockwise.

Downstream of the mount section 13, the pipe 10 may include an outlet filter 14. Outlet filter 14 collects the dust particles not retained by the water retention device 19, e.g., coalescer device.

Between the inlet filter 11 and the mount section 13, the pipe 10 has an injector 12 in the form of an injection nozzle or mist system that is capable of homogenously loading the airflow with a desired quantity of dust particles and/or droplets of water. In this manner, the airflow crossing the water retention device 19, e.g., coalescer device, to be tested may be loaded with dust particles and/or droplets of water, according to desired quantities. In one example, the injection nozzle 12 brings together the functions of loading the air flow with dust particles and droplets of water. However, an alternative embodiment two injection nozzles, one of them intended to emit dust particles and the other to emit droplets of water, may be envisaged.

The test system may include a first drain 15 to harvest water produced by the accumulation of the droplets stopped by the water retention device 19 to be tested and which fall by gravity. This drain is located on the lower wall of the test pipe 10, immediately before the mount section 13. The form of the test pipe 10 is thus selected in order to favor the collection of droplets of water by the drain 15. For this purpose, the pipe 10 comprises a hole immediately upstream of the mount section 13 of the water retention device 19, forming an angle 13 with the horizontal line. The section of the pipe is thus locally extended towards the bottom in a manner as to favor the collection and evacuation of the droplets of water Immediately downstream of mount section 13, the hole narrows down, forming an angle α with the horizontal line. This geometry favors the evacuation of the droplets through the first drain 15.

A second drain 16 is aimed at harvesting the water from the droplets not stopped by the water retention device 19, e.g., coalescer device, and which fall by gravity due to the specific weight of the droplets. Second drain 16 is also located on the lower wall of the test pipe 10. In the second drain 16, the form of the test pipe 10 is selected, as for the first drain 15, in order to favor the harvesting and evacuation of the droplets by the drain 16.

The first and second drains allow comparing by difference between the upstream and downstream quantify of water (e.g., using a water quantity sensor for water from each drain), and knowing the quantity of water injected by injector 12, the quantity of water retained in the mount section 13, i.e., in the water retention device 19. Thus, they allow measuring the quantity of water retained by the device in the mount section.

The pipe 10 also provides a way of measuring the distribution of sizes of dust and water particles in the air flow at various locations. In other words, it allows determining the distribution of sizes of the dust particles and distribution of sizes of the droplets, i.e., on the one hand, distribution of dust particles according to the size, and on the other hand, distribution of droplets according to size. In particular, test pipe 10 includes a plurality of sensors, e.g., 17, 18 among others. For example, a first sensor 17 may be located just upstream of the mount section 13, and a second sensor 18 may be located just downstream of it. Sensors 17, 18 measure the distribution of sizes of the dust and water particles present in air. In this manner, it is possible to measure the distribution of sizes of the dust and water particles present in air upstream and downstream of the water retention device, 19 e.g., coalescer device. As will be described herein, this information may be processed to characterize the size of the particles retained by the water retention device 19, e.g., coalescer device.

As indicated above, a water retention device 19 in the form of a coalescer device 19 is intended to be placed upstream of a gas turbine compressor. The coalescer device's function is to stop the droplets of water present in the air flow before they enter and damage the compressor blades. In addition to retaining water, the coalescer device 19 may retain dust particles. This phenomenon is harmful as it may lead to considerable impedance loss and shut down of the turbine. Thus, a test as described herein aims at characterizing the performance of a coalescer device in its function of stopping the droplets of water by retaining at least the dust particles. Thus, the process according to embodiments of the invention can aid in selecting an appropriate filter to be fitted in an installation integrating a gas turbine.

Figure 2:
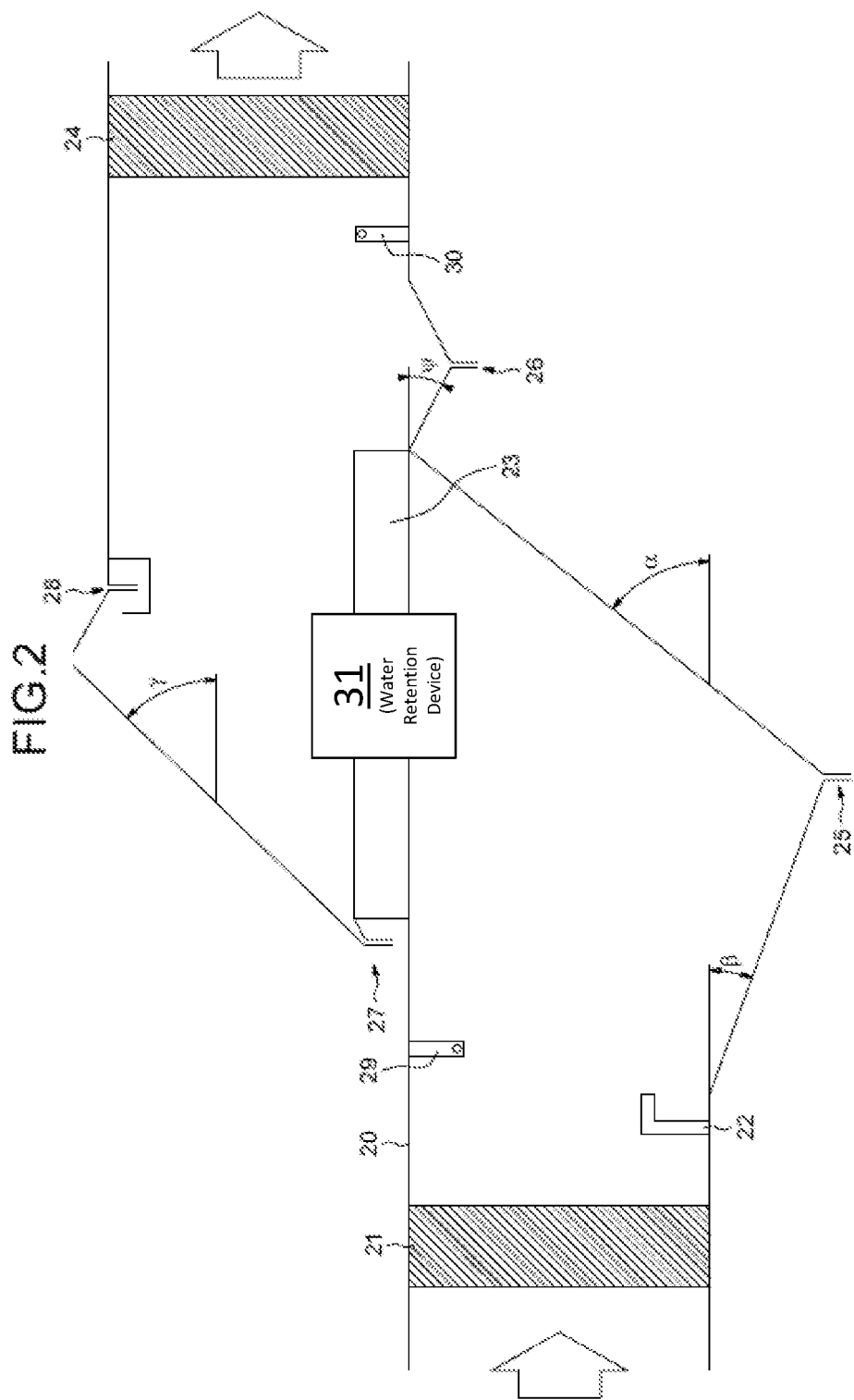
FIG. 2 represents a schematic view of a system for characterization of a water retention device according to a second embodiment.

FIG. 2 schematically represents a sectional view of a system for characterization of a water retention device 31, e.g., coalescer device, according to a second embodiment. In this embodiment, the water retention device 31, e.g., coalescer device, is fitted horizontally.

As in the embodiment described in reference to FIG. 1, the system comprises a test pipe 20 used to set up an airflow. The pipe 20 may include an inlet filter 21, whose function is to ensure that the air flow at the inlet is devoid of dust particles. The pipe 20 also includes a mount section 23 for a water retention device 31, e.g., coalescer device, to be tested. In this embodiment, the mount section 23 and the architecture of the pipe 20 are such that the coalescer device to be tested is fitted in a horizontal position.

In one non-limiting example, the water retention device 31, e.g., coalescer device, may be placed in a manner that it forms an angle with the horizontal line. In particular, the coalescer device 31 may be led to forming an angle with the 45° horizontal line, counter-clockwise.

Pipe 20 may also include an outlet filter 24 located downstream of the mount section 23 of the coalescer to be tested. Its function is to collect the dust particles or water not retained by the coalescer device 31. The system comprises an injector 22, e.g., in the form of an injection nozzle 22. It is located upstream of the mount section 23. As in the embodiment described above, its function is to inject the dust particles and droplets of water in the airflow upstream of the mount section 23.

The pipe 20 also provides a way for measuring the distribution of sizes of dust particles and droplets of water in the air flow at different locations, similar to the measurement methods of the various other embodiments. In particular, the pipe includes a first sensor 29 located upstream of the mount section 23, and a second sensor 30 located downstream of the mount section 23.

Furthermore, the system may include a first drain 25 to harvest the water stopped by the water retention device 31, e.g., coalescer device, to be tested which falls from the device by gravity in the form of larger drops. The water retention device 31 being placed horizontally, the drain 25 is placed on the lower part of the pipe 20, in the area of mount section 23. The form of the pipe 20 is selected in a manner as to favor the collection and evacuation of droplets through the first drain 25. In this regard, the pipe 20 has a hole just upstream of the mount section 23, forming angles 13 and a with the horizontal line. Thus, the pipe section narrows towards the bottom in order to enable evacuation of the droplets through the first drain 25.

The system may include a group of second drains 26, 27 and 28 to harvest the water formed by the droplets not stopped by the water retention device 31, e.g., coalescer device. The water retention device being placed in a horizontal position, the drains 26 and 27 are located on the wall of the test pipe 20 on either side of the mount section 23 and drain 28 is located in the upper part of the pipe 20. The form of the test pipe 20 is selected in a manner as to enable collection of the droplets of water by the group of second drains 26, 27 and 28. For this purpose, the pipe 20 adopts a specific form on either side of the water retention device 31, e.g., coalescer device, and includes chamfers inclined in relation to the horizontal line, according to the angles γ and ψ.

Figure 3:
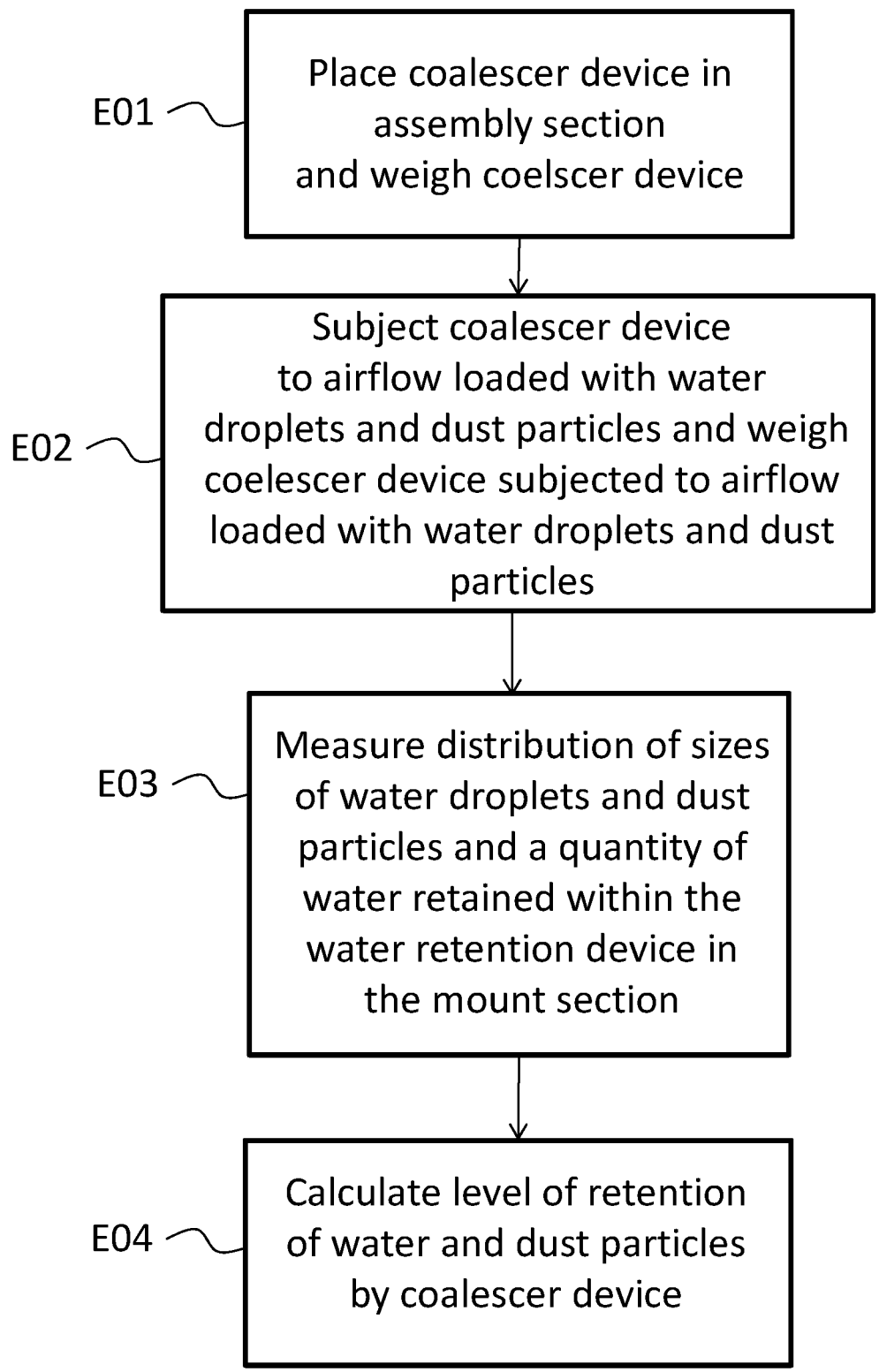
FIG. 3 illustrates a flow diagram of steps of a process for characterization of a water retention device according to an embodiment of the invention.

In FIG. 3, a flow diagram illustrates the steps of a characterization process of a water retention device, e.g., coalescer device. The process is implemented through a test system according to one of the embodiments described above.

In the first step E01, the water retention device, e.g., coalescer device, is placed in the mount section of a test pipe of a test system as described above. For example, with reference to FIG. 1, the water retention device, e.g., coalescer device, is placed in the mount section 13 in a vertical position, i.e., perpendicular to a horizontal airflow.

In a second step E02, the water retention device, e.g., coalescer device, is subjected to an air flow loaded with at least one of droplets of water and dust particles. To create the air flow, a classic fan can be used upstream of the system to force the air into the inlet of the test system. The air flow spreads in the pipe, crossing the filters and the water retention device, e.g., coalescer device. By once again referring to FIG. 1, the air flow passes close to the injector 12, e.g., injection nozzle, of the dust particles and/or droplets of water. Thus, in this manner the water retention device, e.g., coalescer device, is subjected to an airflow loaded with at least one of water and dust particles. This step lasts for a predetermined period. For example, dust of the type of an American Society of Heating, Refrigeration and Air-conditioning Engineers (ASHRAE) standard may be emitted as per a predetermined quantity.

In a third step E03, the distribution of sizes of the dust particles and/or droplets of water present in the air is measured, through sensors 17, 18, at different positions in the test pipe of the system. For example, on the one hand, the distribution of dust particles and droplets of water upstream of the mount section may be measured, and on the other hand, the distribution of these same elements downstream of the mount section may be measured. Also, a quantity of water retained in water retention device in the mount section can be measured, e.g., based on a quantity of water sensed in drains 15, 16 (FIG. 1) and a known amount injected by injector 12.

In a fourth step E04, level of retention of dust and water by the water retention device, e.g., coalescer device, is calculated. For example, the distribution of sizes of dust and water particles may be compared upstream and downstream of the mount section of the water retention device (coalescer device), and the same is carried out for the droplets of water. Based on the two amounts measured, it is possible to quantify a dust and water retention level of the water retention device (coalescer device).

In alternative embodiments, in the second step, the water retention device is subjected to a flow only loaded with dust particles, or a flow only loaded with droplets of water. In these special cases, only the efficiency of the dust filtration and water filtration respectively is characterized. In another embodiment, implementation of a characterization process, in the second step, the water retention device may be subjected to a flow only loaded with droplets of water then the water retention device is subjected to a flow only loaded with dust particles.

In another embodiment, for example, it is possible to implement a characterization process of a water retention device through characterization measures as described above including the following steps: a) The water retention device is placed in the mount section of the system; b) the water retention device is subjected to an air flow loaded with droplets of water; c) the airflow is stopped and the measurement data is collected, i.e., distribution of sizes of droplets of water and the quantity of water stopped by the water retention device; d) the filter is dried; e) steps b), c) and d) are repeated; f) the dust particles are sent (injected into and transmitted by the airflow) to the water retention device; g) the dispatch (injection) of dust is stopped; h) step e) is repeated; i) the dispatch of droplets of water is stopped and the dust particles are sent to the water retention device; j) step e) is repeated; k) the dispatch of the droplets of water is stopped and the dust particles are sent in order to load the water retention device at, for example, 250 Pascal (Pa); and l) steps a) to e) are repeated.

In another embodiment, the water retention device may be weighed before and after the subjecting to the airflow (E02). In this case, the calculating (E04) may include calculating a difference between a first mass of the water retention device measured before the submitting and a second mass of the water retention device measured after the submitting to determine the dust and water retention level.

Thus, thanks to the characterization measure which has just been described, comprising a test pipe, an injector for the dust particles and/or droplets of water, it is possible to qualify the efficiency of the water and dust filtration of a water retention device for its use, for example, upstream of a turbine compressor of the electric power plant.

The invention claimed is:

1. A test system for a water retention device, the system comprising:
 a test pipe including a mount section for holding the water retention device to be tested;
 an injector to inject, upstream of the mount section, an air flow loaded with at least one of dust and droplets of water;
 a first plurality of sensors for determining a distribution of sizes of the at least one of the dust and water particles, and a quantity of water upstream of the mount section;
 a second plurality of sensors, downstream of the mount section, for determining a distribution of sizes of the at least one of the dust and water particles, and a quantity of water retained in the mount section; and
 a calculator receiving the measured distribution of dust and water from the at least one of the plurality of sensors to determine therefrom a dust and water retention level in the water retention device.

2. The system according to claim 1, wherein the injector disperses just dust in the air upstream of the mount section of the water retention device.

3. The system according to claim 1, wherein the injector includes a mist system placed in the pipe upstream of the mount section of the water retention device.

4. The system according to claim 1, wherein the injector includes an injection nozzle.

5. The system according to claim 1, wherein the at least one sensor includes a sensor capable of measuring the distribution of sizes of dust and water particles in the test pipe.

6. The system according to claim 1, wherein the pipe includes a first drain upstream of the mount section and at least one second drain downstream of the mount section.

7. The system according to any claim 6, wherein the at least one second drain includes a group of second drains downstream of the mount section.

8. The system according to claim 1, wherein the water retention device is disposed vertically in the mount section.

9. The system according to claim 1, wherein the water retention device is disposed horizontally in the mount section.

10. The system according to claim 1, wherein the test pipe includes at least one of an inlet filter and an outlet filter.

11. The system according to claim 1, wherein the water retention device includes a coalescer device.

12. A process for characterization of a water retention device, through a system according to claim 1, the method comprising:
 placing the water retention device in the mount section of the test pipe;
 subjecting the water retention device to an airflow loaded with at least one of dust particles and droplets of water;
 measuring, using a plurality of sensors, a distribution of sizes of the at least one of dust particles and droplets of water in the airflow located before and after the water retention device, and a quantity of water retained in the water retention device in the mount section; and
 calculating a dust and water retention level of the water retention device.

13. The characterization process according to claim 12, wherein the submitting the water retention device to the airflow loaded with at least one of dust and droplets of water includes submitting the device to an airflow loaded with both dust and droplets of water.

14. The characterization process according to claim 12, further comprising weighing of the water retention device before and after the subjecting to the airflow, wherein the calculating includes calculating a difference between a first mass of the water retention device measured before subjecting the water retention device to the airflow and a second mass of the water retention device measured after subjecting the water retention device to the airflow to determine the dust and water retention level of the water retention device.

* * * * *